United States Patent
Kamon (10) Patent No.: US 11,449,988 B2
(45) Date of Patent: Sep. 20, 2022

(54) MEDICAL IMAGE PROCESSING APPARATUS

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 347 days.

(21) Appl. No.: 16/795,506

(22) Filed: Feb. 19, 2020

(65) Prior Publication Data

US 2020/0184645 A1 Jun. 11, 2020

Related U.S. Application Data

(63) Continuation of application No. PCT/JP2018/032972, filed on Sep. 6, 2018.

(30) Foreign Application Priority Data

Sep. 15, 2017 (JP) .............................. JP2017-177822

(51) Int. Cl.
*G06K 9/00* (2022.01)
*A61B 5/05* (2021.01)
*G06T 7/00* (2017.01)
*A61B 8/00* (2006.01)

(52) U.S. Cl.
CPC ............ *G06T 7/0012* (2013.01); *A61B 8/469* (2013.01)

(58) Field of Classification Search
CPC ................ G06K 9/00; A61B 1/04; A61B 5/05
USPC ....... 382/100, 103, 106, 168, 173, 181, 190, 382/199, 224, 254, 286–291, 305, 312, 382/128–132, 219; 600/327, 410
See application file for complete search history.

(56) References Cited

U.S. PATENT DOCUMENTS

| | | | |
|---|---|---|---|
| 8,064,677 B2 | 11/2011 | Nie et al. | |
| 8,502,861 B2 | 8/2013 | Hirakawa | |
| 8,681,208 B2 | 3/2014 | Yoshino | |
| 8,830,307 B2 | 9/2014 | Hirakawa | |
| 9,129,384 B2 * | 9/2015 | Tanaka | A61B 1/00009 |
| 9,186,051 B2 | 11/2015 | Hirota | |
| 9,898,664 B2 | 2/2018 | Matsuzaki | |
| 10,198,811 B2 | 2/2019 | Kamiyama et al. | |
| 10,223,785 B2 | 3/2019 | Kitamura et al. | |

(Continued)

FOREIGN PATENT DOCUMENTS

| | | |
|---|---|---|
| CN | 101273916 | 10/2008 |
| CN | 103202702 | 7/2013 |

(Continued)

OTHER PUBLICATIONS

"Search Report of Europe Counterpart Application", dated Oct. 5, 2020, p. 1-p. 4.

(Continued)

*Primary Examiner* — Seyed H Azarian
(74) *Attorney, Agent, or Firm* — JCIPRNET (57) ABSTRACT

A medical image processing apparatus having a processor configured to: acquire a plurality of medical images each including a subject image; detect a region of interest for each medical image; determine whether or not a plurality of the regions of interest detected for each medical image are regions including the same target; and count the number of the regions of interest excluding an overlap of the regions determined to include the same target among the plurality of the regions of interest.

22 Claims, 9 Drawing Sheets

(56) References Cited

U.S. PATENT DOCUMENTS

| | | | |
|---|---|---|---|
| 10,244,972 B2 | 4/2019 | Tominaga | |
| 10,331,851 B2* | 6/2019 | Takata | G16H 30/20 |
| 2004/0059215 A1* | 3/2004 | Nishimura | A61B 5/415 600/410 |
| 2005/0171814 A1 | 8/2005 | Kobayashi et al. | |
| 2008/0039692 A1 | 2/2008 | Hirakawa | |
| 2008/0303898 A1 | 12/2008 | Nishimura | |
| 2012/0274754 A1 | 11/2012 | Tsuruoka | |
| 2013/0184537 A1 | 7/2013 | Konuma et al. | |
| 2013/0211217 A1* | 8/2013 | Yamaguchi | A61B 5/742 600/327 |
| 2014/0334698 A1* | 11/2014 | Tanaka | A61B 1/00009 382/128 |
| 2016/0338575 A1* | 11/2016 | Honda | G02B 23/2423 |
| 2017/0091930 A1* | 3/2017 | Kozuka | G16H 30/40 |

FOREIGN PATENT DOCUMENTS

| | | |
|---|---|---|
| JP | 2005137395 | 6/2005 |
| JP | 2005165677 | 6/2005 |
| JP | 2007236957 | 9/2007 |
| JP | 2008061704 | 3/2008 |
| JP | 2008301968 | 12/2008 |
| JP | 2011024727 | 2/2011 |
| JP | 2011110429 | 6/2011 |
| JP | 2011224038 | 11/2011 |
| JP | 2011255006 | 12/2011 |
| JP | 2012070938 | 4/2012 |
| JP | 2012170641 | 9/2012 |
| JP | 2012249936 | 12/2012 |
| JP | 2015032127 | 2/2015 |
| JP | 2015066129 | 4/2015 |
| JP | 2015112431 | 6/2015 |
| JP | 2015181594 | 10/2015 |
| JP | 2016021216 | 2/2016 |
| JP | 2017012665 | 1/2017 |
| KR | 20130100688 | 9/2013 |
| WO | 2006123455 | 11/2006 |
| WO | 2015137016 | 9/2015 |
| WO | 2015141692 | 9/2015 |

OTHER PUBLICATIONS

"Office Action of Japan Counterpart Application" dated Oct. 27, 2020, with English translation thereof, p. 1-p. 10.
"International Search Report (Form PCT/ISA/210) of PCT/JP2018/032972," dated Dec. 4, 2018, with English translation thereof, pp. 1-6.
"Written Opinion of the International Searching Authority (Form PCT/ISA/237) of PCT/JP2018/032972," dated Dec. 4, 2018, with English translation thereof, pp. 1-7.
"Office Action of China Counterpart Application", dated Oct. 11, 2021, with English translation thereof, p. 1-p. 12.
"Office Action of Japan Counterpart Application" with English translation thereof, dated Aug. 17, 2021, p. 1-p. 8.
"Office Action of Europe Counterpart Application", dated Sep. 9, 2021, p. 1-p. 3.
Office Action of Japan Counterpart Application, with English translation thereof, dated Apr. 13, 2021, pp. 1-10.
"Office Action of China Counterpart Application", dated May 7, 2022, with English translation thereof, p. 1-p. 17.

* cited by examiner

MEDICAL IMAGE PROCESSING APPARATUS

CROSS-REFERENCE TO RELATED APPLICATIONS

This application is a Continuation of PCT International Application No. PCT/JP2018/032972 filed on Sep. 6, 2018, which claims priority under 35 U.S.C § 119(a) to Japanese Patent Application No. 2017-177822 filed on Sep. 15, 2017. Each of the above application(s) is hereby expressly incorporated by reference, in its entirety, into the present application.

BACKGROUND OF THE INVENTION

1. Field of the Invention

The present invention relates to a medical image processing apparatus that uses analysis results of medical images.

2. Description of the Related Art

In the related art, a doctor performs diagnosis or the like using an image (hereinafter, referred to as a medical image) obtained from an apparatus relevant to medical care (hereinafter, referred to as a medical apparatus) which acquires the medical image including a subject image as one of determination materials. Needless to say, discrimination of a state of the subject or the like that is performed using the medical image at the time of diagnosis is based on skill, experience, and the like of the doctor.

In recent years, since image analysis technology has advanced, various types of objective information can be acquired from the medical image by analyzing the medical image. For this reason, the medical apparatus that supports discrimination, diagnosis, and the like by presenting an analysis result of the medical image to a doctor or the like has been on the increase. For example, a system that automatically measures the number of lesions in a mammography image is known (JP2011-110429A).

SUMMARY OF THE INVENTION

In the related art, in order to support diagnosis, a region to be noted (hereinafter, referred to as a region of interest) such as a region with a lesion may be detected from the medical image. In addition, in recent years, analysis results of the medical images may be statistically aggregated and used for secondary use such as research purposes. For example, in a case where a large intestine is examined using an endoscope apparatus (a medical apparatus), the number of regions of interest such as a region in which polyps are found and a region in which treatment (a biopsy and the like) should be performed or has been performed is aggregated to be used for research. It is important in development of medicine to aggregate the analysis results of the medical images, but there is a problem that work such as aggregation is burden on the doctor.

An object of the present invention is to provide a medical image processing apparatus which reduces work burden of a doctor by aggregating analysis results of medical images automatically and correctly.

A medical image processing apparatus of the present invention comprises: a medical image acquisition unit that acquires a plurality of medical images each including a subject image; a region of interest detection unit that detects a region of interest for each medical image; a same region of interest determination unit that determines whether or not a plurality of the regions of interest detected for each medical image are regions including the same target; and a region of interest counting unit that counts the number of the regions of interest excluding an overlap using a determination result in the same region of interest determination unit.

It is preferable that the region of interest counting unit clusters the medical images in which the same region of interest is detected, and counts the number of clusters.

It is preferable that the region of interest counting unit counts the number of the regions of interest for each type of the regions of interest.

It is preferable that the type of the region of interest includes a kind, a size, a position in a lumen, a macroscopic morphology, or an endoscopic finding classification of a lesion included in the region of interest.

It is preferable that the type of the region of interest includes a use status of a medicine or a content of treatment.

It is preferable that the medical image processing apparatus further comprises a type determination unit that determines the type of the region of interest using the medical image, wherein the region of interest counting unit counts the number of the regions of interest for each type of the regions of interest, using a determination result relating to the type of the region of interest in the type determination unit.

It is preferable that the number of the regions of interest and an examination time are stored in association with each other.

It is preferable that the examination time includes an insertion time, an extraction time, or both of the insertion time and the extraction time.

It is preferable that the medical image processing apparatus further comprises: a capturing time acquisition unit that acquires a capturing time of the medical image; and an examination time calculation unit that calculates the examination time using the capturing times of two medical images among the plurality of medical images.

It is preferable that the examination time calculation unit calculates the examination time using the capturing time of the medical image obtained by capturing a specific part or position.

It is preferable that the medical image processing apparatus further comprises an examination information acquisition unit that acquires examination information that is information relating to a patient or a doctor, wherein the number of the regions of interest and the examination information are stored in association with each other.

The medical image processing apparatus of the present invention can reduce work burden of a doctor by aggregating analysis results of medical images automatically and correctly.

DESCRIPTION OF THE PREFERRED EMBODIMENTS

First Embodiment

Figure 1:
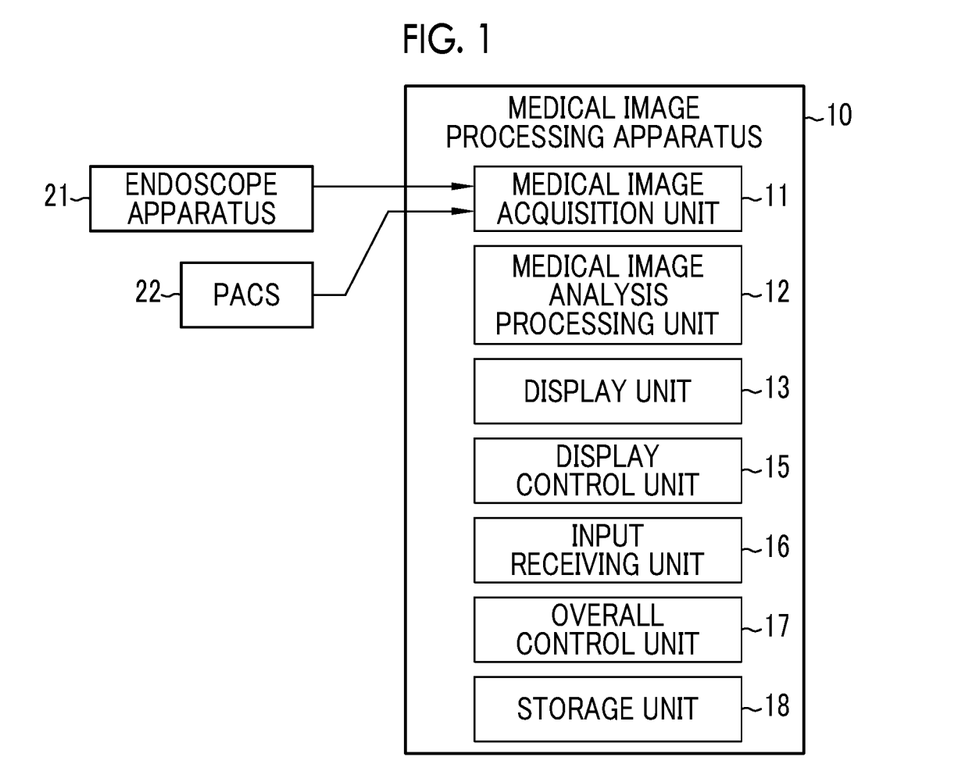
FIG. 1 is a block diagram of a medical image processing apparatus.

As shown in FIG. 1, a medical image processing apparatus 10 comprises a medical image acquisition unit 11, a medical image analysis processing unit 12, a display unit 13, a display control unit 15, an input receiving unit 16, an overall control unit 17, and a storage unit 18.

The medical image acquisition unit 11 acquires a medical image including a subject image, directly from an endoscope apparatus 21 or the like that is a medical apparatus, or through a management system such as a picture archiving and communication system (PACS) 22, or other information systems. Further, the medical image is a still image or a motion picture (a so-called examination motion picture). In a case where the medical image is a motion picture, the medical image acquisition unit 11 can acquire a frame image forming a motion picture after examination as a still image. In addition, in a case where the medical image is a motion picture, display of the medical image includes not only displaying a still image of one representative frame forming the motion picture but also reproducing the motion picture once or multiple times. In addition, the medical image acquired by the medical image acquisition unit 11 includes an image automatically captured by a medical apparatus such as the endoscope apparatus 21 regardless of a capturing instruction of a doctor, in addition to an image captured by a doctor using a medical apparatus such as the endoscope apparatus 21.

In the case of being capable of acquiring a plurality of medical images, the medical image acquisition unit 11 can selectively acquire one or a plurality of medical images among these medical images. In addition, the medical image acquisition unit 11 can acquire a plurality of medical images acquired in a plurality of different examinations. For example, it is possible to acquire one or both of a medical image acquired in an examination performed in the past and a medical image acquired in the latest examination. That is, the medical image acquisition unit 11 acquires a medical image optionally.

In the present embodiment, a plurality of medical images each including a subject image are acquired. More specifically, in a case where a medical image captured in one specific examination is acquired and there are a plurality of medical images captured in one specific examination, a plurality of medical images are acquired out of a series of medical images. In addition, in the present embodiment, the medical image processing apparatus 10 is connected to the endoscope apparatus 21 to acquire a medical image from the endoscope apparatus 21. That is, in the present embodiment, the medical image is an endoscopic image.

Figure 2:
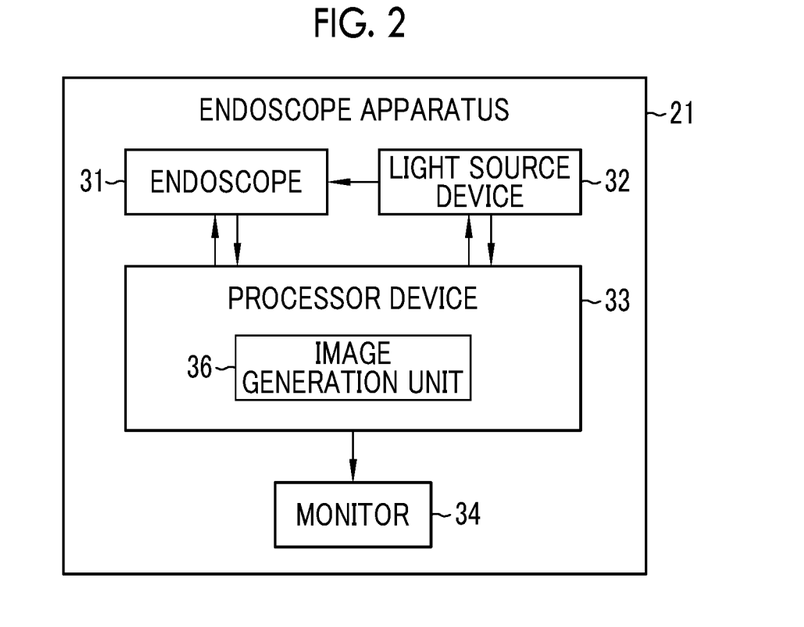
FIG. 2 is a block diagram of an endoscope apparatus.

As shown in FIG. 2, in the present embodiment, the endoscope apparatus 21 to which the medical image processing apparatus 10 is connected has an endoscope 31 that acquires an image by emitting at least one of light in a white wavelength band or light in a specific wavelength band to capture the subject, a light source device 32 that emits illumination light to the inside of the subject through the endoscope 31, a processor device 33, and a monitor 34 for displaying an endoscopic image or the like captured by using the endoscope 31. The light in a specific wavelength band that is used as illumination light by the endoscope 31 is, for example, light in a shorter wavelength band than the green wavelength band. In particular, the light in a specific wavelength band is light in a blue band or a violet band of the visible range. The processor device 33 comprises an image generation unit 36 that generates an endoscopic image. The medical image processing apparatus 10 is connected to the processor device 33. The medical image acquisition unit 11 acquires the endoscopic image directly from the image generation unit 36 of the endoscope apparatus 21.

Figure 3:
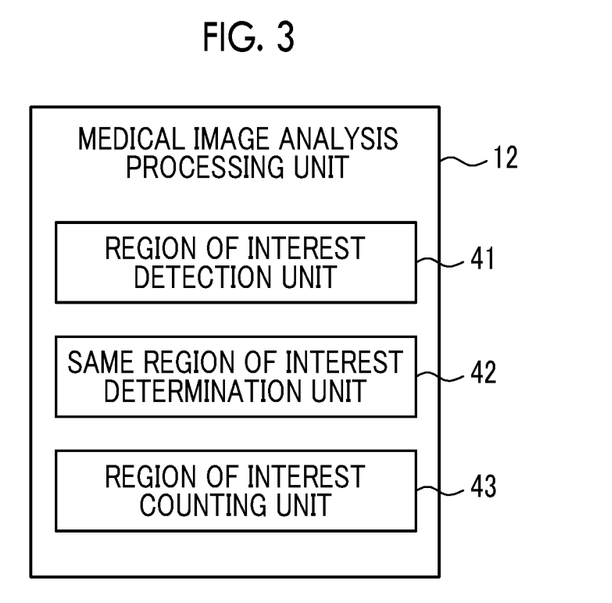
FIG. 3 is a block diagram of a medical image analysis processing unit.

The medical image analysis processing unit 12 performs analysis processing using the endoscopic image acquired by the medical image acquisition unit 11. Specifically, as shown in FIG. 3, the medical image analysis processing unit 12 includes a region of interest detection unit 41, a same region of interest determination unit 42, and a region of interest counting unit 43.

The region of interest detection unit 41 detects the region of interest for each medical image. In this embodiment, regions of interest are respectively detected for a plurality of endoscopic images captured in one examination. The region of interest detected by the region of interest detection unit 41 is a region including a target such as one or a plurality of lesions, a region having a feature of a color or shape different from that of a surrounding tissue, a region in which a medicine is dispersed, or a region in which a treatment (a biopsy, an endoscopic mucosal resection (EMR), an endoscopic submucosal dissection (ESD), or the like) is performed. In a case where the medical image for detecting the region of interest is an endoscopic image, the lesion is, for example, a polyp (a raised lesion), and more specifically, a hyperplastic polyp (HP), a sessile serrated adenoma/polyp (SSA/P), an adenoma, a cancer, or the like. In addition, the region having a feature of a color or shape different from that of the surrounding tissue or the like is a redness, an atrophy, a diverticulum, a treatment mark, or the like of the subject.

The region of interest detection unit 41 can detect a plurality (a plurality of locations) of regions of interest from one medical image. In this case, respective regions of interest may partially overlap with one another. In addition, the region of interest detection unit 41 detects one lesion as one region of interest according to a setting, a kind of a lesion, or the like or detects a portion in which a plurality of lesions are collected, as one region of interest. In addition to this, the region of interest detection unit 41 can detect one or a plurality of kinds of regions of interest (for example, a region including a specific lesion and a region including a lesion having other features) according to a setting. The region of interest detection unit 41 detects the region of interest using a color, a shape, or the like of a subject image reflected in the medical image or one or a plurality of feature amounts (for example, oxygen saturation or the like) calculated using the color, the shape, or the like of the subject image reflected in the medical image. In the present embodiment, the region of interest detection unit 41 detects a polyp or the like, which is a medical image, as a region of interest.

The same region of interest determination unit 42 determines whether or not a plurality of regions of interest detected for each medical image are regions including the same target. The same region of interest determination unit 42 determines whether or not the regions of interest of each medical image include the same target using, for example, a similarity of a color or shape of each medical image or each region of interest, one or a plurality of feature amounts calculated using a color or shape of the subject image included in each medical image or each region of interest, a capturing time of each medical image, a movement of the subject between the medical images (a movement vector indicating an amount and a direction of a movement of the subject), or a determination condition obtained by combining these conditions. For example, in a case where a similarity between the subject images in the regions of interest is high, the same region of interest determination unit 42 can determine that these regions of interest are the same region of interest in which the same target (for example, the same polyp) is detected. In addition, in a case where feature amounts relating to the subject images in the regions of interest or distributions of the feature amounts are similar to each other, the same region of interest determination unit 42 can determine that these regions of interest are the same region of interest in which the same target is detected. In addition, the same region of interest determination unit 42 can determine whether or not a portion reflected in each medical image is the same portion of the subject by taking capturing times of a series of medical images or the movement of the subject into consideration. As a result, the same region of interest determination unit 42 can determine whether or not the regions of interest of each medical image are regions including the same target using a capturing time or movement of the subject.

The region of interest counting unit 43 counts the number of regions of interest excluding an overlap using a determination result in the same region of interest determination unit 42. More specifically, the region of interest counting unit 43 clusters the medical images in which the same region of interest is detected, and counts the number of clusters. As a result, the region of interest counting unit 43 counts the number of regions of interest without an overlap. In clustering performed by the region of interest counting unit 43, one medical image may belong to a plurality of the clusters. For example, in a case where a polyp X1 and a polyp X2 that is different from the polyp X1 are reflected in one medical image, this medical image belongs to both of a cluster C-X1 formed in the medical image in which the polyp X1 is reflected and a cluster C-X2 formed in the medical image in which the polyp X2 is reflected, simultaneously. Further, the region of interest counting unit 43 forms clusters (classification items) optionally according to the determination result in the same region of interest determination unit 42 so as to cluster the medical images. That is, one or a plurality of medical images form a cluster as a result of clustering. Herein, the region of interest counting unit 43 can cluster the medical images by classifying the medical images into a cluster that is predetermined by a setting.

The display unit 13 is a display for displaying the medical image acquired by the medical image acquisition unit 11 and an analysis result of the medical image analysis processing unit 12. A monitor or a display included in a device or the like to which the medical image processing apparatus 10 is connected can be shared and used as the display unit 13 of the medical image processing apparatus 10. The display control unit 15 controls a display form of the medical image and the analysis result on the display unit 13.

The input receiving unit 16 receives inputs from a mouse, a keyboard, and other operation devices connected to the medical image processing apparatus 10. An operation of each unit of the medical image processing apparatus 10 can be controlled using the operation devices.

The overall control unit 17 controls the overall operation of each unit of the medical image processing apparatus 10. In a case where the input receiving unit 16 receives an operation input using an operation device, the overall control unit 17 controls each unit of the medical image processing apparatus 10 according to the operation input.

The storage unit 18 stores at least the number of regions of interest counted by the region of interest counting unit 43 in a storage device (not shown) such as a memory included in the medical image processing apparatus 10 or a storage device (not shown) included in a medical apparatus such as the endoscope apparatus 21 or the PACS 22.

Figure 4:
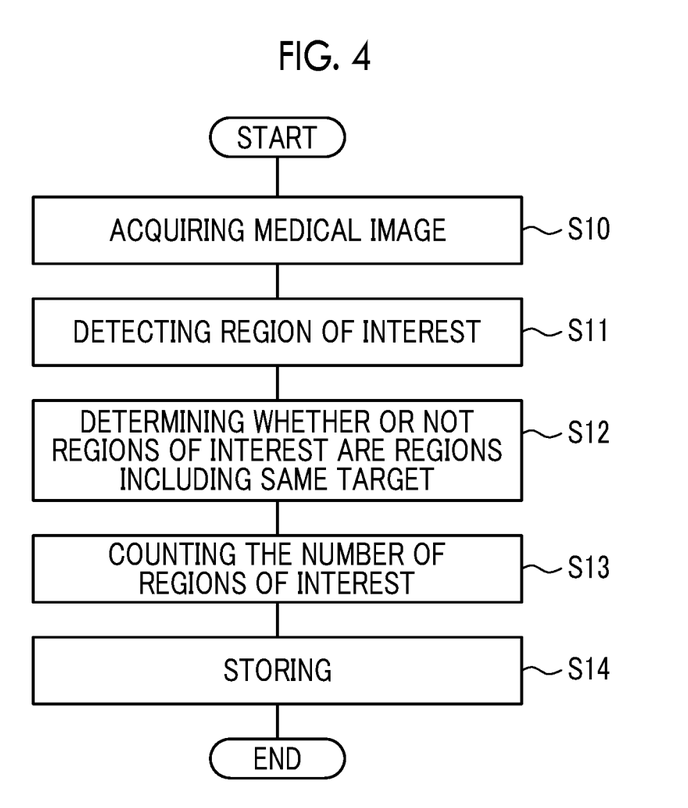
FIG. 4 is a flowchart showing an operation of the medical image processing apparatus.
Figure 5:
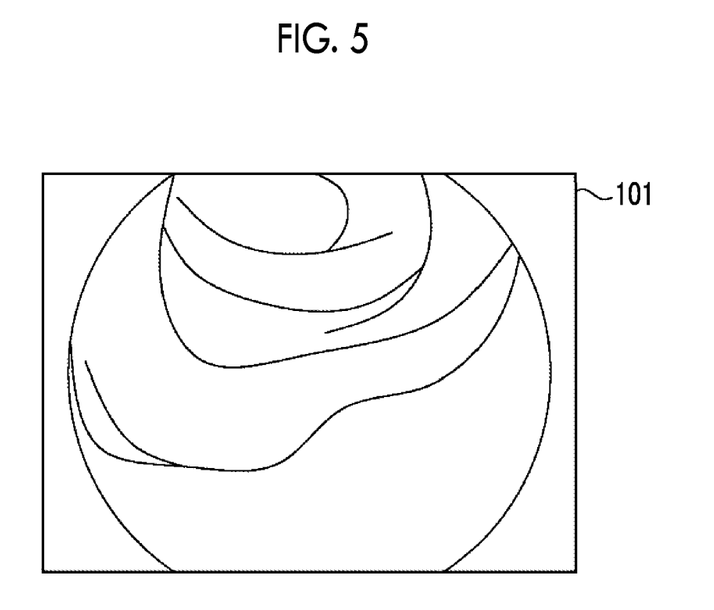
FIG. 5 is an endoscopic image.
Figure 6:
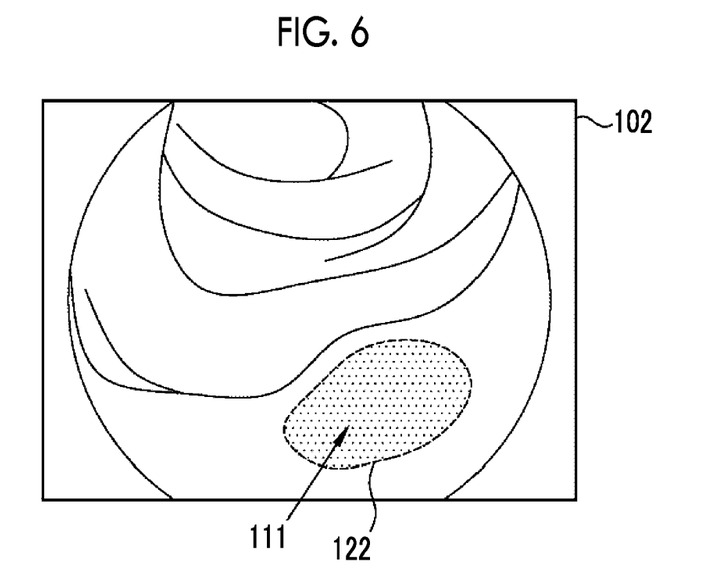
FIG. 6 is an endoscopic image.
Figure 7:
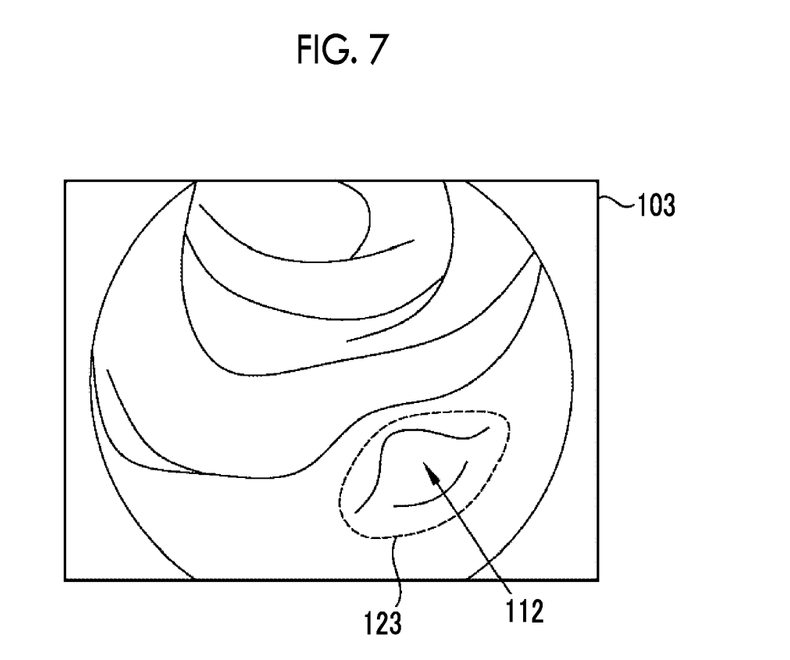
FIG. 7 is an endoscopic image.
Figure 8:
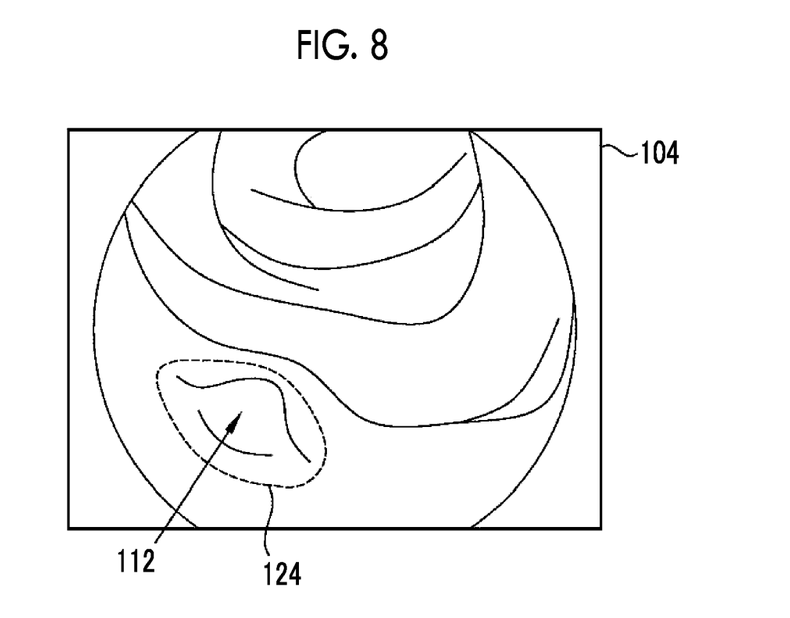
FIG. 8 is an endoscopic image.
Figure 9:
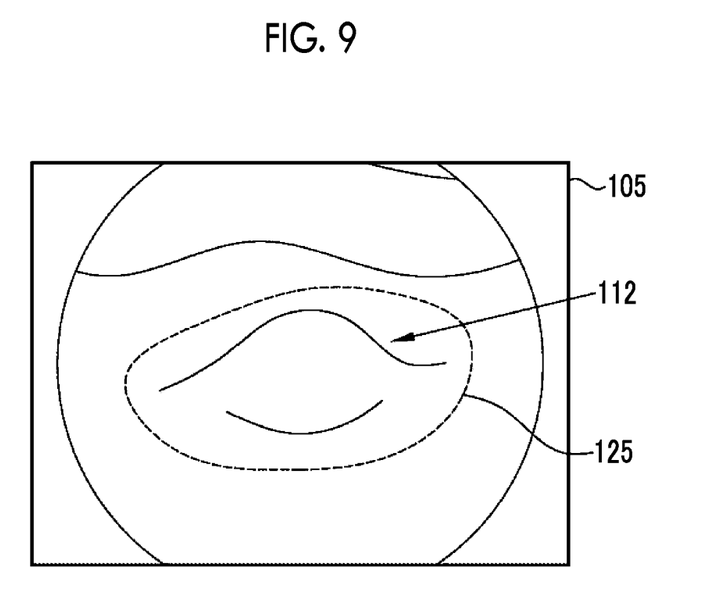
FIG. 9 is an endoscopic image.

Hereinafter, a flow of the operation of the medical image processing apparatus 10 will be described. As shown in FIG. 4, the medical image acquisition unit 11 acquires a plurality of endoscopic images automatically or by manual selection (step S10). In the present embodiment, the medical image acquisition unit 11 acquires endoscopic images 101, 102, 103, 104, and 105 shown in FIGS. 5 to 9 by extracting frame images from a so-called examination motion picture. The endoscopic image 101 shown in FIG. 5 is an endoscopic image obtained by capturing a normal portion without a lesion or the like. The endoscopic image 102 shown in FIG. 6 is, for example, an endoscopic image obtained by capturing a portion with a redness 111. The endoscopic image 103 shown in FIG. 7 is, for example, an endoscopic image obtained by capturing a portion with a polyp 112 (for example, a hyperplastic polyp). An endoscopic image 104 shown in FIG. 8 is an endoscopic image obtained by capturing the polyp 112 from another angle, and an endoscopic image 105 shown in FIG. 9 is an endoscopic image obtained by capturing the polyp 112 with enlargement.

In a case where the medical image acquisition unit 11 acquires the endoscopic images 101, 102, 103, 104, and 105 that are medical images, the region of interest detection unit 41 detects a region of interest for each of the endoscopic images 101, 102, 103, 104, and 105 (step S11). Since the endoscopic image 101 does not include a lesion or the like, the region of interest detection unit 41 executes processing for detecting the region of interest (region of interest detection processing), but does not detect the region of interest as a result (see FIG. 5). Since the endoscopic image 102 includes the redness 111, the region of interest detection unit 41 detects a portion of the redness 111 as a region of interest 122. Since the endoscopic image 103 includes the polyp 112, the region of interest detection unit 41 detects a portion of the polyp 112 as a region of interest 123. Similarly, the region of interest detection unit 41 detects a portion of the polyp 112 as a region of interest 124 in the endoscopic image 104, and detects a portion of the polyp 112 as a region of interest 125 in the endoscopic image 105.

In a case where the region of interest detection unit 41 detects the regions of interest 122, 123, 124, and 125, including the case where no region of interest is detected, for each of the endoscopic images 101, 102, 103, 104, and 105, the same region of interest determination unit 42 determines whether or not these regions of interest 122, 123, 124, and 125 are regions including the same target (step S12). In the present embodiment, the region of interest 122 is a region in which the redness 111 is detected, and the regions of interest 123, 124, and 125 are regions in which the polyp 112 is detected. For this reason, the same region of interest determination unit 42 determines that the region of interest 122 is different from any of the other regions of interest 123, 124, and 125. The regions of interest 123, 124, and 125 are regions in which the same polyp 112 is detected, although the regions are different from one another in a position in the image, a capturing angle (a capturing direction), an enlargement rate, or the like. Therefore, the same region of interest determination unit 42 determines that the region of interest 123 of the endoscopic image 103, the region of interest 124 of the endoscopic image 104, and the region of interest 125 of the endoscopic image 105 are regions including the same target.

Figure 10:
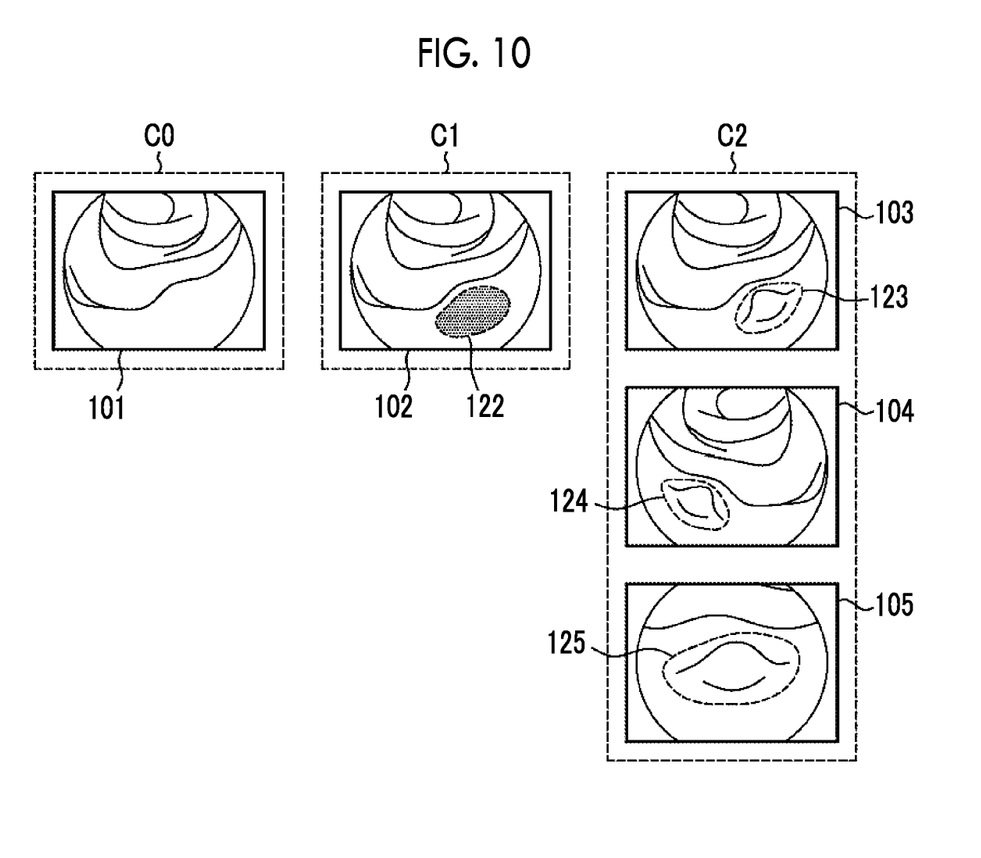
FIG. 10 is an explanatory diagram showing a method of clustering endoscopic images and counting regions of interest.

In a case where the same region of interest determination unit 42 determines whether or not the regions of interest 122, 123, 124, and 125 detected for each of the endoscopic images 101, 102, 103, 104, and 105 are the same, the region of interest counting unit 43 counts the number of regions of interest (step S13). In the case of the present embodiment, as shown in FIG. 10, the region of interest counting unit 43 clusters the endoscopic images 101, 102, 103, 104, and 105 using the determination result of the same region of interest determination unit 42. A cluster C0 is a cluster having an endoscopic image that does not include a region of interest, as an element. Therefore, the endoscopic image 101 belongs to the cluster C0. A cluster C1 is a cluster having an endoscopic image that includes the region of interest 122 in which the redness 111 is detected, as an element. Therefore, the endoscopic image 102 belongs to the cluster C1. A cluster C2 is a cluster having an endoscopic image that includes the regions of interest 123, 124, and 125 in which the polyp 112 is detected, as an element. Therefore, the endoscopic images 103, 104, and 105 belong to the cluster C2.

In a case where the endoscopic images 101, 102, 103, 104, and 105 are clustered, the region of interest counting unit 43 counts the number of clusters formed as a result of clustering. In the case of the present embodiment, as a result of clustering, three clusters of the cluster C0, the cluster C1, and the cluster C2 are formed, but the cluster C0 is a cluster having the endoscopic image 101 that does not include a region of interest, as an element. Therefore, the region of interest counting unit 43 sets the clusters C1 and C2 having the endoscopic images 102, 103, 104, and 105 that includes a region of interest, as an element, as a target of counting, except for the cluster C0. Thereby, the region of interest counting unit 43 can obtain a result that the number of clusters having the endoscopic image that includes a region of interest, as an element, that is, the number of independent regions of interest is two (two kinds), wherein the number of detected rednesses 111 is one and the number of detected polyps 112 is one. The number of independent regions of interest counted by the region of interest counting unit 43 is stored in a predetermined storage device by the storage unit 18 (step S14).

As described above, the medical image processing apparatus 10 can count the number of independent regions of interest by determining whether or not a plurality of regions of interest respectively detected from a plurality of medical images are regions including the same target. Therefore, the medical image processing apparatus 10 can automatically and correctly aggregate the number of rednesses 111 and the number of polyps 112 or the like, which are the analysis results of the medical images. As a result, the medical image processing apparatus 10 can reduce the work burden on the doctor relating to aggregation of the analysis results of the medical images.

Second Embodiment

In the first embodiment, since the number of each of the rednesses 111 and the polyps 112 is counted, the region of interest counting unit 43 counts the number of regions of interest for each type of the regions of interest. However, the region of interest counting unit 43 can count the number of regions of interest for each type of the regions of interest in more detail.

Figure 11:
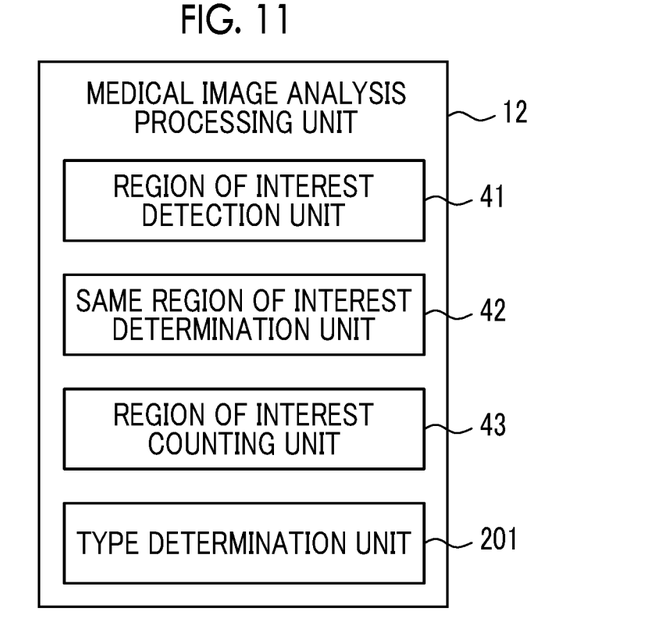
FIG. 11 is a block diagram of a medical image analysis processing unit of a second embodiment.

In this case, as shown in FIG. 11, the medical image analysis processing unit 12 includes a type determination unit 201 in addition to the region of interest detection unit 41, the same region of interest determination unit 42, and the region of interest counting unit 43. The type determination unit 201 determines a type of the region of interest using the medical image. The type of the region of interest refers to a type based on a feature of the subject such as a kind, a size, a position in a lumen with respect to other subjects, a macroscopic morphology, or an endoscopic finding classification of a lesion included in the region of interest, a type of a procedure such as a use status of a medicine or a content of treatment, or a type based on a composite condition obtained by combining these conditions. The endoscopic finding classification includes the narrow-band imaging international colorectal endoscopic (NICE) classification, the Japan narrow band imaging (NBI) expert team (JNET) classification, or the like. The medicine is a coloring agent, a staining agent (such as indigo carmine or pyoktanin), or the like.

In addition, in a case where the type determination unit 201 is provided, the region of interest counting unit 43 counts the number of regions of interest excluding an overlap of regions of interest for each type of the regions of interest using the determination result in the same region of interest determination unit 42 and the determination result relating to the type in the type determination unit 201. In addition, the storage unit 18 stores, in a predetermined storage device, at least the number of regions of interest counted by the region of interest counting unit 43 for each type.

Accordingly, the medical image processing apparatus 10 can automatically and correctly aggregate the analysis results of medical images for each type of lesions. As a result, the medical image processing apparatus 10 can reduce the work burden on the doctor relating to aggregation of the analysis results of the medical images. Specifically, in a case where the type determination unit 201 determines the kind of a lesion, the region of interest counting unit 43 can count, for example, the numbers of hyperplastic polyps, adenomas, and SSA/P, respectively. In addition, in a case where the type determination unit 201 determines a size of a lesion, the region of interest counting unit 43 can count, for example, the number of lesions of 5 mm or more and the number of lesions of less than 5 mm, respectively. In addition, in a case where the type determination unit 201 determines a position in a lumen, the region of interest counting unit 43 can count, for example, the number of lesions in an ascending colon, the number of lesions in a transverse colon, and the number of lesions in a descending colon, respectively. For example, in a case where the type determination unit 201 determines a kind and a size of a lesion, the region of interest counting unit 43 can count, for example, the number of adenomas of 5 mm or more and the number of adenomas of less than 5 mm, respectively. In addition to this, the same applies to a case where the type determination unit 201 determines a macroscopic morphology of a lesion or an endoscopic finding classification of a lesion. In a case where the type determination unit 201 determines a use status of a medicine, the region of interest counting unit 43 can count, for example, the number of regions of interest in which indigo carmine has been dispersed, the number of regions of interest in which pyoktanin has been dispersed, and the number of regions of interest in which the medicine has not been dispersed, respectively. Similarly, in a case where the type determination unit 201 determines a content of treatment, the region of interest counting unit 43 can count the number of regions of interest in which a biopsy has been executed, the number of regions of interest in which EMR has been executed, the number of regions of interest in which ESD has been executed, and the number of regions of interest in which treatment has not been executed, respectively.

Further, in the second embodiment, the type determination unit 201 determines the type of the region of interest, but a doctor can input a part or all of types of the regions of interest. Even in this case, the doctor can automatically and correctly aggregate the analysis results of medical images for each type of lesions by simply inputting the type of the region of interest by selection or the like. Therefore, the medical image processing apparatus 10 can reduce the work burden on the doctor relating to aggregation of the analysis results of the medical images.

Third Embodiment

It is preferable that the number of regions of interest counted by the region of interest counting unit 43 in the medical image processing apparatus 10 of the first embodiment and the second embodiment is stored in association with an examination time. An "examination time" associated with the number of regions of interest is, for example, an insertion time, an extraction time, or both of these in a case of endoscopic examination of a large intestine (a large intestine examination). An insertion time is a time taken for insertion of the endoscope 31, and specifically, is a time from a start of insertion of the endoscope 31 until reaching a cecum. An extraction time is a time taken until an end of examination after reaching a cecum.

Figure 12:
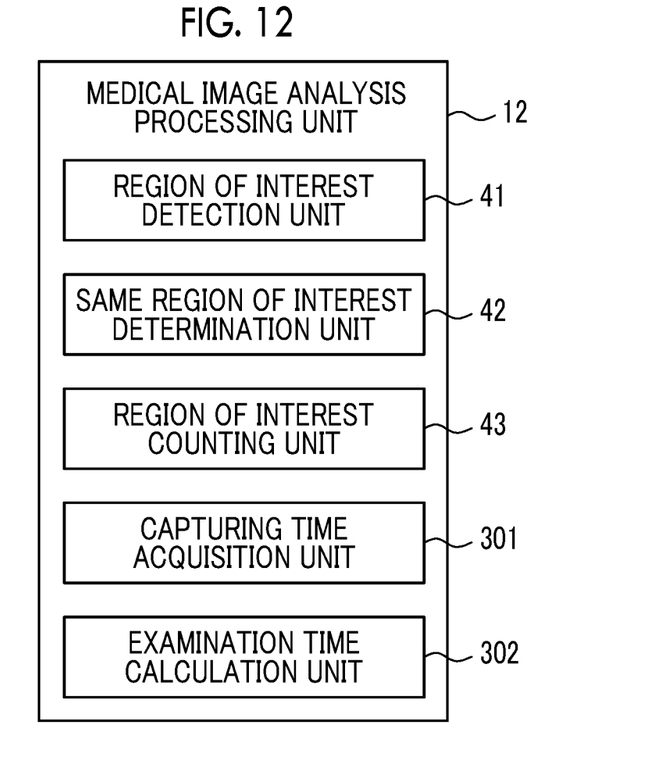
FIG. 12 is a block diagram of a medical image analysis processing unit of a third embodiment.

In a case where the number of regions of interest counted by the region of interest counting unit 43 and an examination time are stored in association with each other, as shown in FIG. 12, the medical image analysis processing unit 12 comprises a capturing time acquisition unit 301 in addition to the region of interest detection unit 41, the same region of interest determination unit 42, and the region of interest counting unit 43. In the present embodiment, the medical image analysis processing unit 12 further comprises an examination time calculation unit 302 in order to store the number of regions of interest in association with an insertion time and an extraction time.

The capturing time acquisition unit 301 acquires a capturing time of the medical image acquired by the medical image acquisition unit 11. In a case where information on a capturing time is recorded in a header or the like of the medical image, the capturing time acquisition unit 301 can acquire a capturing time from the medical image. In addition, in a case where the medical apparatus such as the endoscope apparatus 21 or the PACS 22 holds information on a capturing time, the medical image processing apparatus 10 can acquire a capturing time from the connected medical apparatus or PACS 22. In addition to this, even in a case where the medical image acquisition unit 11 acquires a frame image of the examination motion picture as a medical image, information is obtained from a header or the like of the examination motion picture and a capturing time of each medical image is acquired or calculated.

The examination time calculation unit 302 calculates an insertion time, an extraction time, or both of these using capturing times of two medical images among a plurality of medical images acquired by the medical image acquisition unit 11. In the present embodiment, the examination time calculation unit 302 calculates an insertion time and an extraction time. Specifically, the examination time calculation unit 302 calculates an insertion time from a difference between a capturing time of a medical image captured in a case where insertion of the endoscope 31 is started (a medical image in which an anus or the vicinity thereof is reflected) and a capturing time of a medical image captured in a case where the endoscope 31 reaches a cecum (a medical image in which a cecum is reflected), among a plurality of medical images. Similarly, the examination time calculation unit 302 calculates an extraction time from a difference between a capturing time of a medical image captured in a case where the endoscope 31 reaches a cecum and a capturing time of a medical image captured in a case where the endoscope 31 is extracted from a subject (a medical image in which an anus or the vicinity thereof is reflected), among a plurality of medical images. In the present embodiment, a case of a large intestine examination is illustrated, but the same applies to a case of examining other parts. That is, the examination time calculation unit 302 calculates an examination time using a capturing time of a medical image obtained by capturing a specific part or a specific position of a subject (the vicinity of a change of a part or a frequently occurring part, a position, or the like of a lesion or the like in addition to a cecum or the like). This makes it possible to calculate particularly a practical examination time in an examination in which it is customary to capture a specific part or a specific position of a subject regardless of presence or absence of a lesion.

The storage unit 18 stores the number of regions of interest counted by the region of interest counting unit 43 and an examination time calculated by the examination time calculation unit 302 in a predetermined storage device in association with each other.

As described above, in a case where the number of regions of interest counted by the region of interest counting unit 43 and an examination time are stored in association with each other, it is useful for secondary use such as research.

Further, an examination time can be manually input to the medical image processing apparatus 10 or the like by a doctor or the like. In this case, the capturing time acquisition unit 301 acquires an examination time input by a doctor or the like, and the storage unit 18 stores the number of regions of interest counted by the region of interest counting unit 43 and an examination time input by a doctor or the like in a predetermined storage device in association with each other. In addition, in a case where a doctor or the like manually inputs a start time of the examination, an end time of the examination, or both of these, the examination time calculation unit 302 may calculates a time taken for the examination using a start time of the examination, an end time of the examination, or both of these input by a doctor or the like. For example, in endoscopic examination of a large intestine, a start time of the examination is an insertion start time of the endoscope 31, an end time of the examination is an extraction completion time of the endoscope 31, and these are usually items input by a doctor or the like. In addition to this, in a case where a doctor or the like can manually input a capturing time of the medical image, the capturing time acquisition unit 301 can acquire a capturing time input by a doctor or the like, and the examination time calculation unit 302 can calculate an examination time using a capturing time input by a doctor or the like.

Fourth Embodiment

In the third embodiment, the number of regions of interest counted by the region of interest counting unit 43 and an examination time are stored in association with each other, but it is preferable that instead of an examination time or in addition to an examination time, the number of regions of interest counted by the region of interest counting unit 43 and examination information are stored in association with each other. Examination information is information relating to a patient or a doctor. For example, an age, a sex, a medical history, a content of treatment for a current lesion or the like of a patient, or the like is examination information. In addition, for example, a name (an identification (ID) or the like), a career, an achievement (the number or the like of cases of medical examining a specific lesion), or the like of a doctor is examination information.

Figure 13:
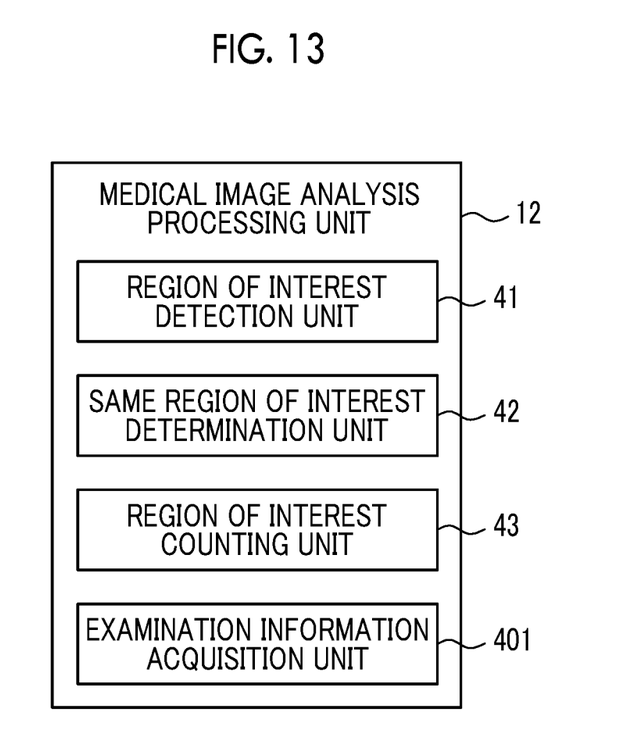
FIG. 13 is a block diagram of a medical image analysis processing unit of a fourth embodiment.

In a case where the number of regions of interest counted by the region of interest counting unit 43 and examination information are stored in association with each other, as shown in FIG. 13, the medical image analysis processing unit 12 comprises an examination information acquisition unit 401 in addition to the region of interest detection unit 41, the same region of interest determination unit 42, and the region of interest counting unit 43. The examination information acquisition unit 401 acquires examination information that is information relating to a patient or a doctor. Then, the storage unit 18 stores the number of regions of interest counted by the region of interest counting unit 43 and examination information acquired by the examination information acquisition unit 401 in a predetermined storage device in association with each other.

As described above, in a case where the number of regions of interest counted by the region of interest counting unit 43 and examination information are stored in association with each other, it is useful for secondary use such as research. In addition, in a case where the number of regions of interest counted by the region of interest counting unit 43 and examination information relating to a doctor are stored in association with each other, it is possible to obtain information serving as an index representing a skill of a doctor who has performed examination.

Further, in the third embodiment, the number of regions of interest counted by the region of interest counting unit 43 and an examination time are stored in association with each other and in the fourth embodiment, the number of regions of interest counted by the region of interest counting unit 43 and examination information are stored in association with each other, but it is preferable that an item to be stored in association with the number of regions of interest counted by the region of interest counting unit 43 can be optionally set for each doctor or for each hospital. In this way, information can be organized and stored without waste according to a purpose of research. The medical image processing apparatus 10 can set an item to be stored in association with the number of regions of interest counted by the region of interest counting unit 43 in the input receiving unit 16.

Figure 14:
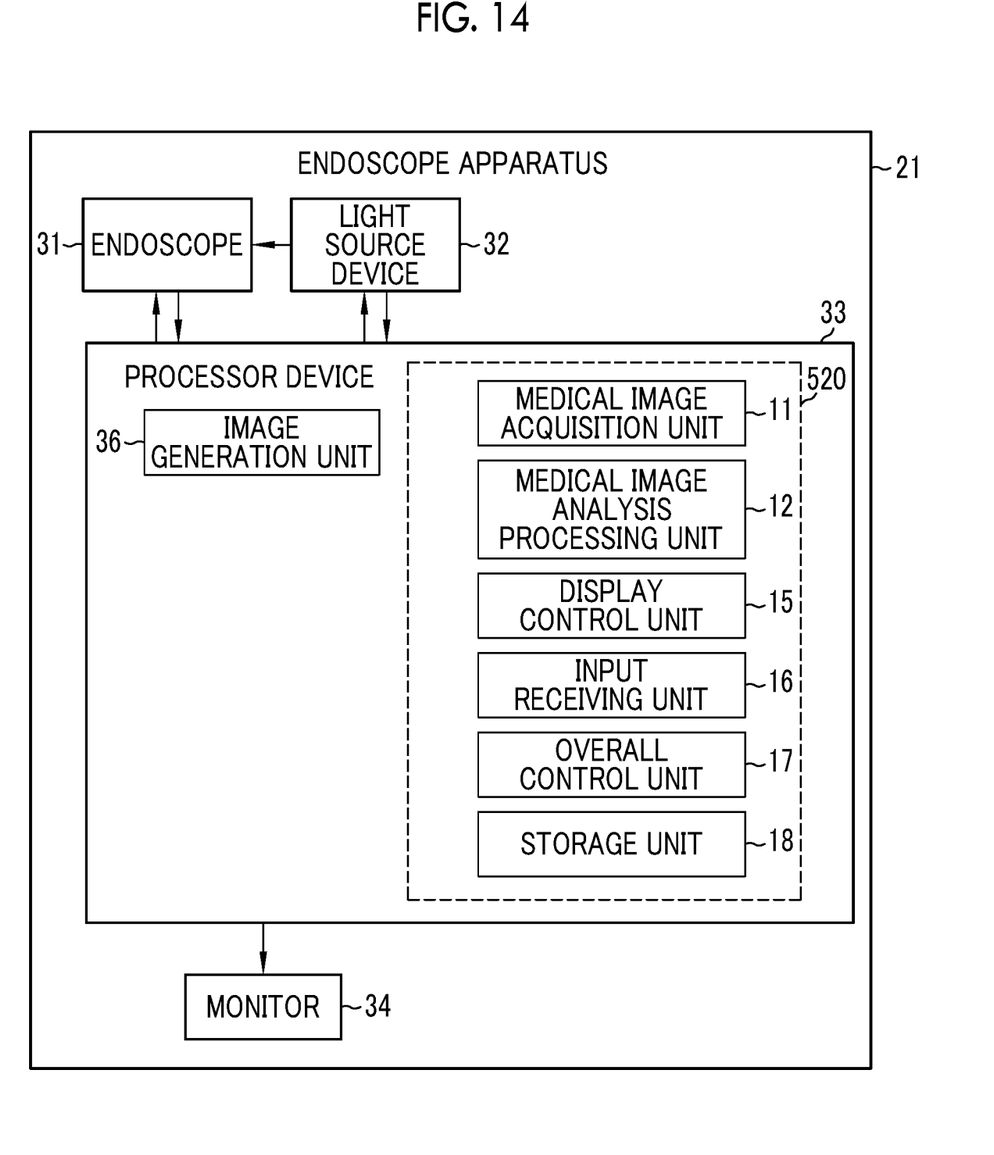
FIG. 14 is a block diagram of an endoscope apparatus including a medical image processing apparatus.

In the embodiment described above, the medical image processing apparatus 10 and the endoscope apparatus 21 are separate apparatuses. However, the endoscope apparatus 21 can include the medical image processing apparatus 10. In this case, as shown in FIG. 14, each unit 520 forming the medical image processing apparatus 10 is provided in the processor device 33. However, since the monitor 34 of the endoscope apparatus 21 can be shared as the display unit 13, it is sufficient to provide each unit other than the display unit 13 in the processor device 33. In addition, a new endoscope apparatus can be configured by all of the medical image processing apparatuses 10 of the above embodiment and other modification examples and the endoscope apparatus 21 shown in FIG. 2.

Basically, the endoscope apparatus 21 is an apparatus for observing the subject in real time. As described above, in a case where the endoscope apparatus 21 includes the medical image processing apparatus 10, detection of a region of interest, determination of the same region of interest, and counting of regions of interest can be performed in a case where an endoscopic image is captured or at any timing.

Figure 15:
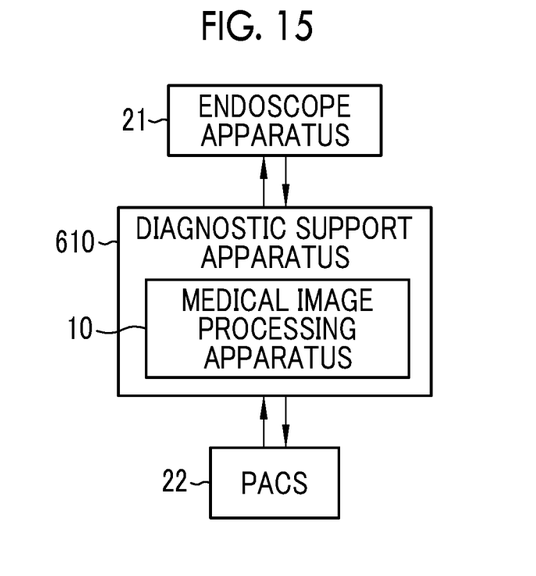
FIG. 15 is a block diagram of a diagnostic support apparatus including a medical image processing apparatus.
Figure 16:
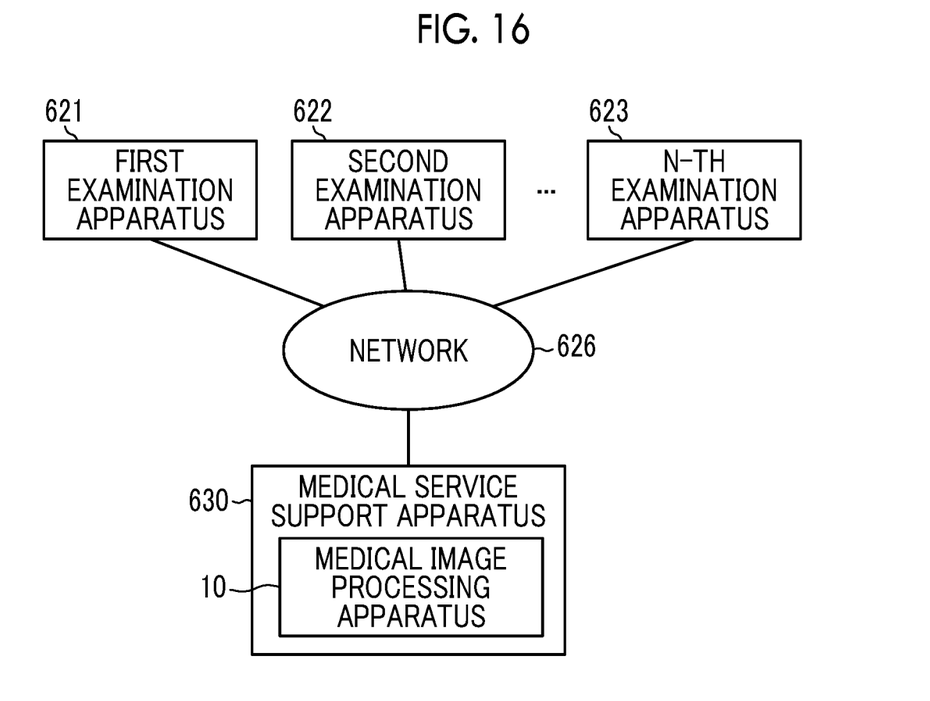
FIG. 16 is a block diagram of a medical service support apparatus including a medical image processing apparatus.

In addition, as shown in FIG. 15, a diagnostic support apparatus 610 used in combination with the endoscope apparatus 21 and other modalities can include the medical image processing apparatuses 10 of the above embodiment and other modification examples. In addition, as shown in FIG. 16, for example, a medical service support apparatus 630 connected to various examination apparatuses including the endoscope apparatus 21, such as a first examination apparatus 621, a second examination apparatus 622, . . . , and an N-th examination apparatus 623, through a certain network 626 can include the medical image processing apparatuses 10 of the above embodiment and other modification examples.

In addition to this, the medical image processing apparatus 10, various apparatuses including the medical image processing apparatus 10, and various apparatuses or systems having a function of the medical image processing apparatus 10 can be used by making the following various changes or the like.

As the medical image, it is possible to use a normal light image obtained by emitting light in a white band or light in a plurality of wavelength bands as light in the white band.

In a case where an image obtained by emitting light in a specific wavelength band is used as the medical image, a band narrower than the white wavelength band can be used as the specific wavelength band.

The specific wavelength band is, for example, a blue band or a green band of a visible range.

In a case where the specific wavelength band is the blue band or the green band of a visible range, it is preferable that the specific wavelength band includes a wavelength band of 390 nm to 450 nm or a wavelength band of 530 nm to 550 nm and that light in the specific wavelength band has a peak wavelength within the wavelength band of 390 nm to 450 nm or the wavelength band of 530 nm to 550 nm.

The specific wavelength band is, for example, a red band of a visible range.

In a case where the specific wavelength band is the red band of a visible range, it is preferable that the specific wavelength band includes a wavelength band of 585 nm to 615 nm or a wavelength band of 610 nm to 730 nm and that light in the specific wavelength band has a peak wavelength within the wavelength band of 585 nm to 615 nm or the wavelength band of 610 nm to 730 nm.

The specific wavelength band can include, for example, a wavelength band in which light absorption coefficients of oxygenated hemoglobin and reduced hemoglobin are different, and light in the specific wavelength band can have a peak wavelength in the wavelength band in which light absorption coefficients of oxygenated hemoglobin and reduced hemoglobin are different.

In a case where the specific wavelength band includes a wavelength band in which the light absorption coefficients of oxygenated hemoglobin and reduced hemoglobin are different and light in the specific wavelength band has a peak wavelength in the wavelength band in which the light absorption coefficients of oxygenated hemoglobin and reduced hemoglobin are different, it is preferable that the specific wavelength band includes a wavelength band of 400±10 nm, 440±10 nm, 470±10 nm, or 600 nm to 750 nm and that light in the specific wavelength band has a peak wavelength within the wavelength band of 400±10 nm, 440±10 nm, 470±10 nm, or 600 nm to 750 nm.

In a case where the medical image is an in-vivo image of the living body, the in-vivo image can have information on fluorescence emitted from the fluorescent material in the living body.

In addition, as the fluorescence, fluorescence obtained by emitting excitation light having a peak wavelength of 390 nm to 470 nm to the inside of the living body can be used.

In a case where the medical image is an in-vivo image of the living body, the wavelength band of infrared light can be used as the specific wavelength band described above.

In a case where the medical image is an in-vivo image of the living body and the wavelength band of infrared light is used as the specific wavelength band described above, it is preferable that the specific wavelength band includes a wavelength band of 790 nm to 820 nm or 905 nm to 970 nm and that light in the specific wavelength band has a peak wavelength within the wavelength band of 790 nm to 820 nm or 905 nm to 970 nm.

The medical image acquisition unit 11 can have a special light image acquisition section that acquires a special light image having a signal in a specific wavelength band on the basis of a normal light image obtained by emitting light in a white band or light in a plurality of wavelength bands as light in the white band. In this case, the special light image can be used as the medical image.

The signal in a specific wavelength band can be obtained by calculation based on the color information of RGB or CMY included in the normal light image.

It is possible to comprise a feature amount image generation unit that generates a feature amount image by calculation based on at least one of the normal light image obtained by emitting light in a white band or light in a plurality of wavelength bands as light in the white band or the special light image obtained by emitting light in a specific wavelength band. In this case, the feature amount image can be used as the medical image.

In the endoscope apparatus 21, a capsule endoscope can be used as the endoscope 31. In this case, the light source device 32 and a part of the processor device 33 can be mounted in the capsule endoscope.

In the above embodiment and modification examples, hardware structures of processing units for executing various kinds of processing, such as the medical image acquisition unit 11, the medical image analysis processing unit 12, each unit forming the medical image analysis processing unit 12, the display control unit 15, the input receiving unit 16, the overall control unit 17, and the image generation unit 36, are various processors shown below. The various processors include a central processing unit (CPU) that is a general-purpose processor that functions as various processing units by executing software (program), a programmable logic device (PLD) that is a processor whose circuit configuration can be changed after manufacture, such as field programmable gate array (FPGA), a dedicated electrical circuit that is a processor having a dedicated circuit configuration for executing various types of processing, and the like.

One processing unit may be configured by one of various processors, or may be configured by a combination of two or more processors of the same type or different types (for example, a combination of a plurality of FPGAs or a combination of a CPU and an FPGA). In addition, a plurality of processing units may be configured by one processor. As an example of configuring a plurality of processing units by one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, the hardware structure of these various processors is an electrical circuit (circuitry) in the form of a combination of circuit elements, such as semiconductor elements.

EXPLANATION OF REFERENCES

10: medical image processing apparatus
11: medical image acquisition unit
12: medical image analysis processing unit
13: display unit
15: display control unit
17: overall control unit
18: storage unit
21: endoscope apparatus
22: PACS
31: endoscope
32: light source device
33: processor device
34: monitor
36: image generation unit
41: region of interest detection unit
42: same region of interest determination unit
43: region of interest counting unit
101, 102, 103, 104, 105: endoscopic image
111: redness
112: polyp
122, 123, 124, 125: region of interest
201: type determination unit
301: capturing time acquisition unit
302: examination time calculation unit
401: examination information acquisition unit
520: each unit forming medical image processing apparatus
610: diagnostic support apparatus
621: first examination apparatus
622: second examination apparatus
623: N-th examination apparatus
626: network
630: medical service support apparatus
C0, C1, C2: cluster

What is claimed is:

1. A medical image processing apparatus comprising:
a processor configured to:
acquire a plurality of medical images each including a subject image;
detect a region of interest for each medical image;
determine whether or not a plurality of the regions of interest detected for each medical image are regions including the same target; and
count the number of the regions of interest excluding an overlap of the regions determined to include the same target among the plurality of regions of interest,
wherein the processor is configured to count the number of the regions of interest for each type of the regions of interest, and the type of the region of interest includes a kind, a size, a position in a lumen, a macroscopic morphology, or an endoscopic finding classification of a lesion included in the region of interest.

2. The medical image processing apparatus according to claim 1,
wherein the processor is configured to cluster the medical images in which the same region of interest is detected, and count the number of clusters.

3. The medical image processing apparatus according to claim 2,
wherein the type of the region of interest includes a use status of a medicine or a content of treatment.

4. The medical image processing apparatus according to claim 2,
wherein the processor is further configured to determine the type of the region of interest using the medical image, and
count the number of the regions of interest for each type of the regions of interest determined.

5. The medical image processing apparatus according to claim 2,
wherein the processor is further configured to store the number of the regions of interest and an examination time in association with each other.

6. The medical image processing apparatus according to claim 1,
wherein the type of the region of interest includes a use status of a medicine or a content of treatment.

7. The medical image processing apparatus according to claim 1,
wherein the processor is further configured to determine the type of the region of interest using the medical image, and
count the number of the regions of interest for each type of the regions of interest determined.

8. The medical image processing apparatus according to claim 1,
wherein the processor is further configured to store the number of the regions of interest and an examination time in association with each other.

9. The medical image processing apparatus according to claim 8,
wherein the examination time includes an insertion time, an extraction time, or both of the insertion time and the extraction time.

10. The medical image processing apparatus according to claim 8,
wherein the processor is further configured to acquire a capturing time of the medical image; and calculate the examination time using the capturing times of two medical images among the plurality of medical images.

11. The medical image processing apparatus according to claim 10,
wherein the processor is configured to calculate the examination time using the capturing time of the medical image obtained by capturing a specific part or position.

12. The medical image processing apparatus according to claim 1,
wherein the processor further is configured to acquire examination information that is information relating to a patient or a doctor, and store the number of the regions of interest and the examination information in association with each other.

13. An endoscope apparatus, comprising:
the medical image processing apparatus as claimed in claim 1; and
an endoscope connected to the medical image processing apparatus and configured to acquire the subject image.

14. A medical image processing apparatus comprising:
a processor configured to:
acquire a plurality of medical images each including a subject image;
detect a region of interest for each medical image;
determine whether or not a plurality of the regions of interest detected for each medical image are regions including the same target;
count the number of the regions of interest excluding an overlap of the regions determined to include the same target among the plurality of the regions of interest;
store the number of the regions of interest and an examination time in association with each other;
acquire a capturing time of the medical image; and
calculate the examination time using the capturing times of two medical images among the plurality of medical images, wherein the processor calculates the examination time using the capturing time of the medical image obtained by capturing a specific part or position.

15. The medical image processing apparatus according to claim 14,
wherein the processor is configured to cluster the medical images in which the same region of interest is detected, and count the number of clusters.

16. The medical image processing apparatus according to claim 14,
wherein the processor is configured to count the number of the regions of interest for each type of the regions of interest.

17. The medical image processing apparatus according to claim 16,
wherein the type of the region of interest includes a kind, a size, a position in a lumen, a macroscopic morphology, or an endoscopic finding classification of a lesion included in the region of interest.

18. The medical image processing apparatus according to claim 16,
wherein the type of the region of interest includes a use status of a medicine or a content of treatment.

19. The medical mage processing apparatus according to claim 16,
wherein the processor is further configured to determine the type of the region of interest using the medical image, and
count the number of the regions of interest for each type of the regions of interest determined.

20. The medical image processing apparatus according to claim 14, wherein the examination time includes an insertion time, an extraction time, or both of the insertion time and the extraction time.

21. The medical image processing apparatus according to claim 14,
wherein the processor is further configured to acquire examination information that is information relating to a patient or a doctor, and store the number of the regions of interest and the examination information in association with each other.

22. A medical image processing method comprising:
acquiring a plurality of medical images each including a subject image by a processor;
detecting a region of interest for each medical image by the processor;
determining whether or not a plurality of the regions of interest detected for each medical image are regions including the same target by the processor; and
counting the number of the regions of interest excluding an overlap of the regions determined to include the same target among the plurality of the regions of interest by the processor,
wherein the processor is configured to count the number of the regions of interest for each type of the regions of interest, and the type of the region of interest includes a kind, a size, a position in a lumen, a macroscopic morphology, or an endoscopic finding classification of a lesion included in the region of interest.

* * * * *